United States Patent [19]
Zanini-Fisher et al.

[11] Patent Number: 6,131,438
[45] Date of Patent: Oct. 17, 2000

[54] METHOD OF OPERATING A CALORIMETRIC GAS SENSOR

[75] Inventors: Margherita Zanini-Fisher, Bloomfield Hills; Jacobus H. Visser, Farmington Hills; E. M. Logothetis, Birmingham, all of Mich.

[73] Assignee: Ford Global Technologies, Inc., Dearborn, Mich.

[21] Appl. No.: 08/772,660

[22] Filed: Dec. 20, 1996

[51] Int. Cl.[7] .............................. G01N 7/00; G01N 27/26; G01N 25/20
[52] U.S. Cl. ............................ 73/23.32; 422/51; 204/427
[58] Field of Search ................................ 73/23.31, 23.32; 422/51, 98; 204/427

[56] References Cited

U.S. PATENT DOCUMENTS

| | | | |
|---|---|---|---|
| 4,305,724 | 12/1981 | Micko | 23/232 E |
| 4,399,684 | 8/1983 | Advani et al. | |
| 4,538,575 | 9/1985 | Chujo et al. | 123/440 |
| 4,541,899 | 9/1985 | Mase et al. | 204/1 T |
| 4,542,640 | 9/1985 | Clifford . | |
| 4,627,269 | 12/1986 | Forster et al. | |
| 4,880,519 | 11/1989 | Wang et al. | 204/425 |
| 5,265,417 | 11/1993 | Visser et al. | |
| 5,448,905 | 9/1995 | Stetter et al. | 73/31.05 |
| 5,527,446 | 6/1996 | Kosek et al. | |
| 5,596,975 | 1/1997 | Thomas et al. | 123/686 |
| 5,898,101 | 4/1999 | Lyle et al. | 73/23.02 |

FOREIGN PATENT DOCUMENTS

| | | |
|---|---|---|
| WO 9300581 | 1/1993 | European Pat. Off. . |
| 37 36 200 | 5/1989 | Germany . |

OTHER PUBLICATIONS

R. Aigner et al., "Sensors and Actuators" B. 18–19 (1994) pp. 143–147.

Bisio et al, Encycolpedia of Energy Technology and the Enviroment vol. 2, Wiley & Sons, pp. 1326, 1334–1336, unknown.

Sensors and Actuators, B Chem, Col 33, #1–3 Jul. 1996, 151–155/Aigner et al.

*Primary Examiner*—Hezron Williams
*Assistant Examiner*—Jay L. Politzer
*Attorney, Agent, or Firm*—Lorraine S. Melotik

[57] ABSTRACT

A method of operating a calorimetric gas sensor by modulating its operating temperature includes the steps of heating a sensing element and a reference element of a calorimetric gas sensor to a first temperature between a predetermined minimum temperature and a light-off temperature of the sensing element, modulating the heating of the sensing element and reference element between a second temperature above the light-off temperature and the first temperature to produce an alternating current (AC) output, and measuring the AC sensor output of the frequency of modulation.

6 Claims, 1 Drawing Sheet

METHOD OF OPERATING A CALORIMETRIC GAS SENSOR

BACKGROUND OF THE INVENTION

1. Field of the Invention

The present invention relates generally to gas sensors and, more specifically, to a method of operating a calorimetric gas sensor for improved accuracy and detection limit.

2. Description of the Related Art

Calorimetric gas sensors are potentially useful for measuring on-board the concentration of combustibles in automotive exhaust systems and for correlating increased levels of combustibles with deterioration of the hydrocarbon (HC) efficiency of an automotive three-way-catalyst (TWC). An example of such a calorimetric gas sensor is disclosed in U.S. Pat. No. 5,451,371 to Zanini-Fisher et al. This patent discloses a silicon-based microcalorimetric gas sensor. The detection limit of the microcalorimetric gas sensor was found under laboratory conditions to be sufficiently high to be able to measure hydrocarbon concentration levels in exhaust gas of newer automotive vehicles. However, when these sensors are directly mounted in the automotive exhaust system, the detection limit is reduced. First, the sensor noise increases in a high-velocity, turbulent flow because the effect of local thermal fluctuations, that are not compensated by the differential nature of the sensor, becomes more important. Secondly, the intrinsic zero-offset of the sensor output which derives from small differences in resistance between a reference element and the catalytically active element (i.e., the sensing element) can be larger than signals associated with typical hydrocarbon concentration levels present after the TWC. Although the zero-offset can be reduced by accurate trimming operations, any small resistance drift induced by ageing compromises the long term accuracy of the sensor. Therefore, there is a need in the art to improve the accuracy and the detection limit of calorimetric gas sensors for measuring exhaust gas constituents.

SUMMARY OF THE INVENTION

Accordingly, the present invention is a method of operating a calorimetric gas sensor by modulating its operating temperature to produce an AC output. The method includes the steps of heating the sensing element and the reference element of a calorimetric gas sensor to a first temperature between a predetermined minimum temperature and a light-off temperature of the catalyst on the sensing element. The method also includes the step of modulating the heating of the sensing element and the reference element between a second temperature above the light-off temperature and the first temperature to produce an alternating current (AC) output. The method further includes the step of measuring the AC sensor output at the frequency of modulation.

One advantage of the present invention is that a method is provided of operating a calorimetric gas sensor by modulating its operating temperature. The advantage of the present invention is that, by modulating the temperature of the catalytic sensing element, an AC output is produced in the sensor which is proportional to combustibles reacting with oxygen to be measured and largely independent of the intrinsic DC zero-offset of the sensor. Yet another advantage of the present invention is that the sensor detection limit is greatly increased because the AC sensor output can be measured using frequency or phase-sensitive detection techniques which permit a much higher rejection of background thermal fluctuations that are not spatially correlated.

Other features and advantages of the present invention will be readily appreciated as the same becomes better understood after reading the subsequent description when considered in connection with the accompanying drawings.

DESCRIPTION OF THE PREFERRED EMBODIMENT(S)

One embodiment of a calorimetric gas sensor is disclosed in U.S. Pat. No. 5,451,371 to Zanini-Fisher et al., the disclosure of which is hereby incorporated by reference. The calorimetric gas sensor includes a pair of polysilicon plates attached to a bulk silicon frame with polysilicon arms. Each of the polysilicon plates contains two platinum resistors, one used as a resistive temperature detector (RTD) and the other used as a heater. These heaters are capable of heating the plates to an equal temperature substantially higher than that of the environment. The thermal response time of the sensor is approximately twelve (12) to thirteen (13) milliseconds (ms) when the surrounding gas is at room temperature.

One of the polysilicon plates, the sensing element, has a catalytic layer disposed thereon, while the other, the reference element, has no catalyst and is used for temperature compensation. When combustibles that react with oxygen (e.g., CO,HC) are present in a gas sample, the exothermic reactions of these molecules on the catalytic layer raises the temperature of the sensing element above that of the reference element. A measurement of the temperature difference between the two elements provides a measure of the concentration of the combustibles in the gas sample. Such temperature difference is derived by measuring the resistance difference of the two RTDs, one on the reference element and the other on the sensing element. For instance, as explained in U.S. Pat. No. 5,451,371, when the RTDs are connected in a Wheatstone bridge, the sensor output is given by the bridge imbalance voltage. It should be appreciated that the calorimetric gas sensor is conventional and known in the art.

The above-described calorimetric gas sensor is sensitive to combustibles above a temperature for which the reaction rate in the catalytic layer of the sensing element is sufficiently fast to generate a detectable temperature rise on the sensing element. As the catalyst temperature is increased, the reaction rate becomes faster than the diffusion rate of the combustibles reacting with oxygen to the surface and the temperature rise on the sensing element levels off. A light-off temperature is defined as the temperature at which the conversion rate of reactants or combustibles reacting with oxygen on the sensor is half of the maximum value. This temperature depends on the catalyst used for the catalytic layer and on the nature of the combustibles to be oxidized. For example, for propylene oxidized on a thin film of palladium, the light-off temperature is between 260° C. and 280° C. Since reaction rates are exponentially dependent on temperature, they change rapidly within a few degrees of the light-off temperature, especially when the activation energy for the process is small.

Figure 1:
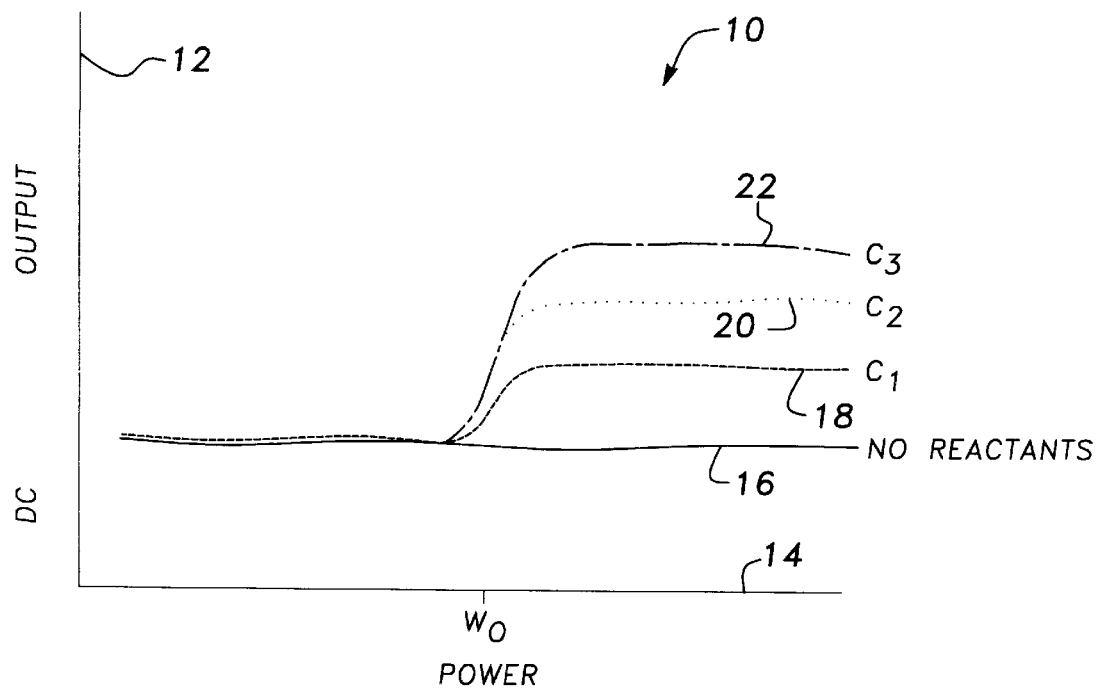
FIG. 1 is a schematic representation of the output of a calorimetric gas sensor when it is heated with constant power.

Referring to FIG. 1, a graph 10 of DC output 12 versus power 14 is illustrated for the above-described calorimetric gas sensor when exposed to a gas stream at room temperature. The sensor DC output is a function of the temperature to which the sensing element and reference element of the sensor are heated. Such temperature is a function of constant (e.g., DC) power dissipated in the heaters for different values of reactant concentration. $W_0$ is the power corresponding to the catalyst light-off temperature for a specific reactant or combustible reacting with oxygen. When no combustibles reacting with oxygen are present, the sensor DC output is essentially constant as a function of power as represented by the line 16. At low power, the sensor DC output does not change when the sensor is exposed to different concentrations of reactants. However, above $W_0$, which corresponds to the power needed to increase the plate temperature above the light-off temperature of the catalyst of the sensing element, the sensor DC output suddenly increases and then remains constant as represented by line 18 for a first gas concentration $C_1$, line 20 for a higher second gas concentration $C_2$ and line 22 for an even higher third gas concentration $C_3$.

According to the present invention, the temperature of the above-described calorimetric gas sensor is modulated by using the following method. The method includes the step of applying direct current (DC) power to the heaters for the sensing element and the reference element to heat the sensing element and reference element to a first temperature between a predetermined minimum temperature and a light-off temperature of the sensing element. For example, to detect propylene with a catalyst made of a palladium (Pd) film, the first temperature can be 240° C. The method includes the step of superimposing an additional time dependent power to the heaters for the sensing element and reference element to modulate the heating and temperature of the sensing element and reference element between a second temperature above the light-off temperature and the first temperature.

Figure 2:
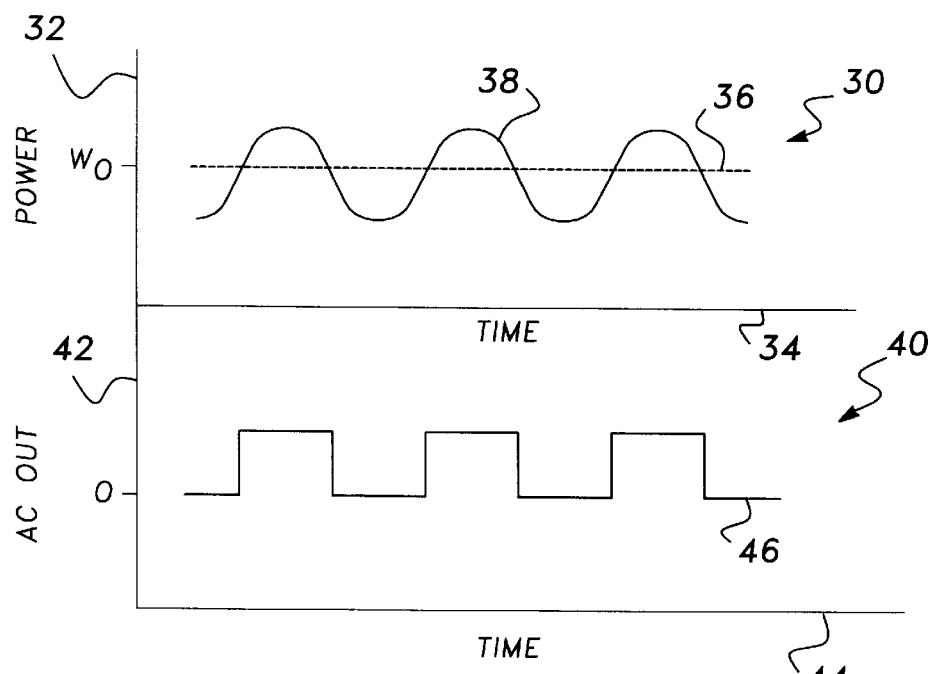
FIG. 2 is a schematic representation of the output of a calorimetric gas sensor when it is heated by a combination of constant and time dependent power.

Referring to FIG. 2, a graph 30 of power 32 versus time 34 is illustrated for the above-described calorimetric gas sensor when exposed to a gas stream. Line 36 represents $W_0$ and line 38 represents the power dissipated through the heaters for a small modulation about $W_0$. Since the thermal response time of the sensor is equal or less than 13 ms, an appreciable temperature modulation can be achieved by modulating the power even at one hundred Hertz (100 Hz). For on-board exhaust gas sensing applications, modulating the sensor output at frequencies of fifty (50) to one hundred (100) Hertz (Hz) greatly increases the rejection of unwanted signals from uncorrelated temperature fluctuations over the sensor. For example, if power to the heaters becomes momentarily larger than $W_0$, the sensing element and reference element will be monetarily heated above the light-off temperature, when the sensor becomes active and produces a signal output. As soon as the power is reduced below $W_0$, the sensor output decreases.

As illustrated in FIG. 2, a graph 40 of AC output 42 versus time 44 is illustrated for the above-described calorimetric gas sensor. The AC sensor output as a function of time is represented by the line 46. To produce a sensor output as given by line 46, a combination of constant (e.g., DC) and time dependent (e.g., AC) power can be used so that the constant power is used to keep the plate temperature just below the light-off temperature and the time dependent power is used to produce a smaller temperature modulation across the light-off temperature. In this way, any thermal mismatch between the two plates which produces a small temperature difference between the reference element and the sensing element that is not related to the reactant concentration, is minimized. It should be appreciated that if only time dependent power is dissipated in the heaters, such that the power changes from zero to a maximum value, the temperature of the plates will change at the same frequency between approximately ambient temperature and a maximum value.

The present invention has been described in an illustrative manner. It is to be understood that the terminology which has been used is intended to be in the nature of words of description rather than of limitation.

Many modifications and variations of the present invention are possible in light of the above teachings. Therefore, within the scope of the appended claims, the present invention may be practiced other than as specifically described.

What is claimed is:

1. A method of operating a calorimetric gas sensor by modulating its operating temperature, said method consisting of the steps of:

providing a calorimetric gas sensor having a sensing element and a reference element;

allowing diffusion of a gas including combustibles to react with the sensing element;

heating the sensing element and the reference element of the calorimetric gas sensor to a first temperature between a predetermined minimum temperature and a light-off temperature of the sensing element defined as the temperature at which the conversion rate of combustibles reacting with oxygen on the calorimetric gas sensor is half of the maximum value;

modulating the heating of the sensing element and reference element to vary the temperature of the calorimetric gas sensor continuously between a second temperature above the light-off temperature and the first temperature to produce an alternating current (AC) sensor output; and measuring the AC sensor output at the frequency of modulation.

2. A method as set forth in claim 1 wherein said step of heating comprises applying direct current (DC) power to heaters for the sensing element and reference element to heat the sensing element and reference element to the first temperature.

3. A method as set forth in claim 1 wherein said step of modulating comprises superimposing a time dependent power to heaters for the sensing element and reference element to modulate the temperature of the sensing element and reference element between the second temperature and first temperature.

4. A method as set forth in claim 1 wherein said step of measuring comprises measuring at the frequency of modulation using frequency or phase-sensitive detection techniques.

5. A method as set forth in claim 1 wherein the modulation frequency is between 0.01 Hz and 100 Hz.

6. A method of modulating temperature of a calorimetric gas sensor, said method consisting of the steps of:

providing a calorimetric gas sensor having a sensing element and a reference element;

allowing diffusion of a gas including combustibles to react with the sensing element;

applying direct current (DC) power to heaters for the sensing element and the reference element of the calorimetric gas sensor for heating the sensing element and reference element to a first temperature between a predetermined minimum temperature and a light-off temperature of the sensing element defined as the temperature at which the conversion rate of combustibles reacting with oxygen on the calorimetric gas sensor is half of the maximum value;

superimposing a time dependent power to heaters for the sensing element and reference element for modulating the heating of the sensing element and reference element to vary the temperature of the calorimetric gas sensor continuously between a second temperature above the light-off temperature and the first temperature to produce an alternating current (AC) sensor output; and measuring the AC sensor output at the frequency of modulation.

* * * * *